United States Patent
Kuroda

(10) Patent No.: US 8,764,912 B2
(45) Date of Patent: Jul. 1, 2014

(54) METHOD OF CLEANING NOZZLE AND DEVICE FOR CLEANING NOZZLE

(75) Inventor: Akihisa Kuroda, Shizouka (JP)

(73) Assignee: Beckman Coulter, Inc., Brea, CA (US)

( * ) Notice: Subject to any disclaimer, the term of this patent is extended or adjusted under 35 U.S.C. 154(b) by 81 days.

(21) Appl. No.: 12/881,118

(22) Filed: Sep. 13, 2010

(65) Prior Publication Data

US 2011/0017238 A1    Jan. 27, 2011

Related U.S. Application Data

(63) Continuation of application No. PCT/JP2009/054628, filed on Mar. 11, 2009.

(30) Foreign Application Priority Data

Mar. 17, 2008    (JP) .................... 2008-068305

(51) Int. Cl.
     *B08B 3/00*      (2006.01)

(52) U.S. Cl.
     USPC ..................... 134/166 R; 134/199

(58) Field of Classification Search
     USPC ... 134/166 R, 169 R, 169 C, 170, 171, 166 C
     See application file for complete search history.

(56) References Cited

U.S. PATENT DOCUMENTS

| | | | | |
|---|---|---|---|---|
| 4,730,631 A | * | 3/1988 | Schwartz | 134/155 |
| 5,133,373 A | * | 7/1992 | Hoffman et al. | 134/88 |
| 5,186,194 A | * | 2/1993 | Kitajima | 134/154 |
| 6,422,248 B1 | * | 7/2002 | Furst et al. | 134/22.11 |

FOREIGN PATENT DOCUMENTS

| | | | |
|---|---|---|---|
| JP | 62-242858 A | 10/1987 | |
| JP | 62242858 A | * 10/1987 | G01N 35/02 |
| JP | 04-105066 A | 4/1992 | |
| JP | 2003-145077 A | 5/2003 | |

* cited by examiner

*Primary Examiner* — Jason Ko
(74) *Attorney, Agent, or Firm* — Kilpatrick Townsend & Stockton LLP

(57) ABSTRACT

The present invention provides a nozzle cleaning method and a nozzle cleaning device which allow to surely perform cleaning of a dispensing nozzle and which allow reduction in cleaning time. For this purpose, a nozzle cleaning method for cleaning a dispensing nozzle (50) for suctioning and discharging a liquid includes: a first cleaning step in which, after termination of dispensing, an inner wall surface of the dispensing nozzle (50) is cleaned in an upper portion of a storage tank (62) overflowed with a cleaning liquid (L2) by discharging a liquid for preload (L1); and a second cleaning step in which at least an outer wall surface is cleaned by lowering and immersing the dispensing nozzle (50) into the storage tank (62) overflowed with the cleaning liquid (L2).

18 Claims, 10 Drawing Sheets

FIG. 6

(a) Liquid for preload L1 is discharged — ON from $t_1$ to $t_3$ (b) Storage tank 62 is overflowed — ON from $t_1 t_2$ to $t_3 t_4 t_5 t_6$; ON from $t_7 t_8$ (c) Dispensing nozzle 50 is raised/lowered — Lowering $t_5$ to $t_7$; $t_9$ Raising $t_{11}$ (d) Cleaning liquid L2 is exhausted — ON at $t_{10}$ (a) Liquid for preload L1 is discharged (b) Storage tank 62 is overflowed (c) Dispensing nozzle 50 is raised/lowered (d) Means for supplying cleaning liquid to be ejected 61

(e) Cleaning liquid L2 is exhausted

METHOD OF CLEANING NOZZLE AND DEVICE FOR CLEANING NOZZLE

CROSS-REFERENCE TO RELATED APPLICATIONS

This application is a continuation of International Application No. PCT/JP2009/054628, filed Mar. 11, 2009, which claims benefit of priority to Japanese Application No. 2008-068305, filed Mar. 17, 2008, the disclosures of each are herein incorporated by reference.

TECHNICAL FIELD

The present invention relates to a nozzle cleaning method for cleaning a dispensing nozzle for suctioning and discharging a liquid and a nozzle cleaning device.

BACKGROUND ART

Conventionally, an automatic analyzer for analyzing a sample such as blood or urine includes a nozzle cleaning device for cleaning a dispensing nozzle in order to prevent carry-over which affects results of analysis as a result of carrying a previously-dispensed sample adhered to the dispensing nozzle over a sample subsequently dispensed. Such a nozzle cleaning device is disposed on a track where the dispensing nozzle moves, between a position where a sample is suctioned and a position where the sample is discharged, and is configured to supply the dispensing nozzle with a cleaning liquid. In a nozzle cleaning method using such a nozzle cleaning device, after suctioning and discharging the sample and completing dispensing, the dispensing nozzle is moved to the position of the nozzle cleaning device, the cleaning liquid is supplied to this dispensing nozzle, and the dispensing nozzle is cleaned.

In the nozzle after dispensing, a small amount of the sample remains, and if the dispensing nozzle is cleaned in a cleaning device in which a cleaning liquid is stored, the cleaning liquid is contaminated by the sample remaining in the dispensing nozzle. Thus, when a carry-over request level is high, a large amount of cleaning liquid is necessary for the cleaning process and the cleaning time is also long. In order to solve this, a method has been proposed in which a waste tank is installed adjacent to a cleaning tank and cleaning is performed after discarding a residual sample to the waste tank (see, for example, Patent Document 1).

Patent Document 1: Japanese Laid-Open Publication No. 2003-145077

DISCLOSURE OF THE INVENTION

Problem to be Solved by the Invention

However, since the dispensing nozzle is caused to perform predetermined operations in two positions, in the waste tank and the cleaning tank, time required for raising/lowering operation of the dispensing nozzle and a time for moving from the waste tank to the cleaning tank are added to the cleaning time. As a result, longer cleaning time is required than in a cleaning operation performed only in the cleaning tank. Thus, application of a two-tank cleaning device to an automatic analyzer which requires speeding up and improvement in performance is not efficient.

The present invention has been completed in view of the foregoing, and aims to provide a nozzle cleaning method and a nozzle cleaning device which surely perform cleaning of a dispensing nozzle and which allow reduction in cleaning time.

Means for Solving the Problem

In order to solve the aforementioned problem and achieve the aforementioned purpose, a nozzle cleaning method of the present invention for cleaning a dispensing nozzle for suctioning and discharging a liquid is characterized in that the method includes: a first cleaning step in which, after termination of dispensing, an inner wall surface of the dispensing nozzle is cleaned in an upper portion of a storage tank overflowed with a cleaning liquid by discharging a liquid for preload; and a second cleaning step in which at least an outer wall surface of the dispensing nozzle is cleaned by lowering and immersing the dispensing nozzle into the storage tank overflowed with the cleaning liquid.

Furthermore, the nozzle cleaning method of the present invention is characterized in that, in the aforementioned invention, the overflow of the storage tank in the first cleaning step is started instantaneously before, when, or after the liquid for preload discharged from the dispensing nozzle for cleaning the inner wall surface falls and reaches the storage tank.

Furthermore, the nozzle cleaning method of the present invention is characterized in that, in the aforementioned invention, the overflow of the storage tank in the first cleaning step is stopped after termination of discharging the liquid for preload from the dispensing nozzle for cleaning the inner wall surface, after the discharged liquid for preload falls and reaches the storage tank.

Furthermore, the nozzle cleaning method of the present invention is characterized in that, in the aforementioned invention, the overflow of the storage tank in the second cleaning step is restarted after the dispensing nozzle lowers and before a tip of the dispensing nozzle immerses into the storage tank.

Furthermore, the nozzle cleaning method of the present invention is characterized in that, in the aforementioned invention, the overflow of the storage tank in the second cleaning step is stopped before drawing up the dispensing nozzle from the storage tank.

Furthermore, the nozzle cleaning method of the present invention is characterized in that, in the aforementioned invention, a cleaning liquid stored in the storage tank is exhausted after termination of the second cleaning step, after the drawing-up of the dispensing nozzle from the storage tank by raising the dispensing nozzle.

Furthermore, the nozzle cleaning method of the present invention is characterized in that, in the aforementioned invention, the cleaning liquid overflowed from the storage tank is exhausted in the overflow tank in the first cleaning step and the second cleaning step.

Furthermore, the nozzle cleaning method of the present invention is characterized in that, in the aforementioned invention, prior to the second cleaning step, the dispensing nozzle is lowered and entered in a flow path where a cleaning liquid is ejected by a means for supplying cleaning liquid to be ejected in the upper portion of the storage tank overflowed with the cleaning liquid.

Furthermore, the nozzle cleaning device of the present invention for cleaning a dispensing nozzle for suctioning and discharging a liquid is characterized in that the cleaning device includes: a storage tank having an aperture in an upper portion thereof, where the dispensing nozzle is inserted, in which a cleaning liquid is overflowed; an overflow tank where the cleaning liquid overflowed from the storage tank is exhausted; a means for supplying a cleaning liquid to be stored for supplying the cleaning liquid to the storage tank; a controlling means for controlling at least the storage tank to an overflowed condition when a liquid for preload discharged from the dispensing nozzle for cleaning an inner wall surface falls and reaches the storage tank and when a tip of the dispensing nozzle starts to immerse in the storage tank.

Furthermore, the nozzle cleaning device of the present invention for cleaning a dispensing nozzle for suctioning and discharging a liquid is characterized in that, in the aforementioned invention, the aperture of the overflow tank is formed so as to have a slope which inclines downwardly from the aperture of the storage tank.

Furthermore, the nozzle cleaning device of the present invention for cleaning a dispensing nozzle for suctioning and discharging a liquid is characterized in that, in the aforementioned invention, the controlling means controls so that overflow is started before a liquid for preload discharged from the dispensing nozzle for cleaning an inner wall surface falls and reaches the storage tank, and the overflow is stopped after the discharging of the liquid for preload from the dispensing nozzle for cleaning the inner wall surface is terminated and subsequently the discharged liquid for preload falls and reaches the storage tank.

Furthermore, the nozzle cleaning device of the present invention for cleaning a dispensing nozzle for suctioning and discharging a liquid is characterized in that, in the aforementioned invention, the controlling means controls so that overflow is restarted after the dispensing nozzle starts lowering and before the tip of the dispensing nozzle immerses in the storage tank and overflow is stopped before the dispensing nozzle is drawn up from the storage tank.

Furthermore, the nozzle cleaning device of the present invention for cleaning a dispensing nozzle for suctioning and discharging a liquid is characterized in that, in the aforementioned invention, the nozzle cleaning device includes a means for supplying cleaning liquid to be ejected for ejecting a cleaning liquid in a region in the upper portion of the storage tank; and the controlling means controls so that at least the storage tank becomes an overflow condition when cleaning liquid ejected by the means for supplying cleaning liquid to be ejected falls in the storage tank.

Effect of the Invention

According to a nozzle cleaning method of the present invention, when a liquid for preload discharged from a dispensing nozzle for cleaning an inner wall surface together with a residual sample mixes in a cleaning liquid stored in a storage tank, and when the dispensing nozzle with a sample remaining on an outer wall surface thereof is lowered and immersed into the storage tank with the cleaning liquid stored, the cleaning liquid stored in the storage tank is overflowed so as to forcibly exhaust the liquid for preload containing the sample, or the like to an overflow tank together with the cleaning liquid in the storage tank, thereby allowing cleaning of a dispensing nozzle in a single storage tank to allow reduction in cleaning time, and also reducing carry-over of the sample into the storage tank to allow efficient cleaning.

BRIEF DESCRIPTION OF THE DRAWINGS

FIG. 6 is a timing diagram illustrating the cleaning operation in the nozzle cleaning method of the embodiment 1 of the present invention.

Figure 1:
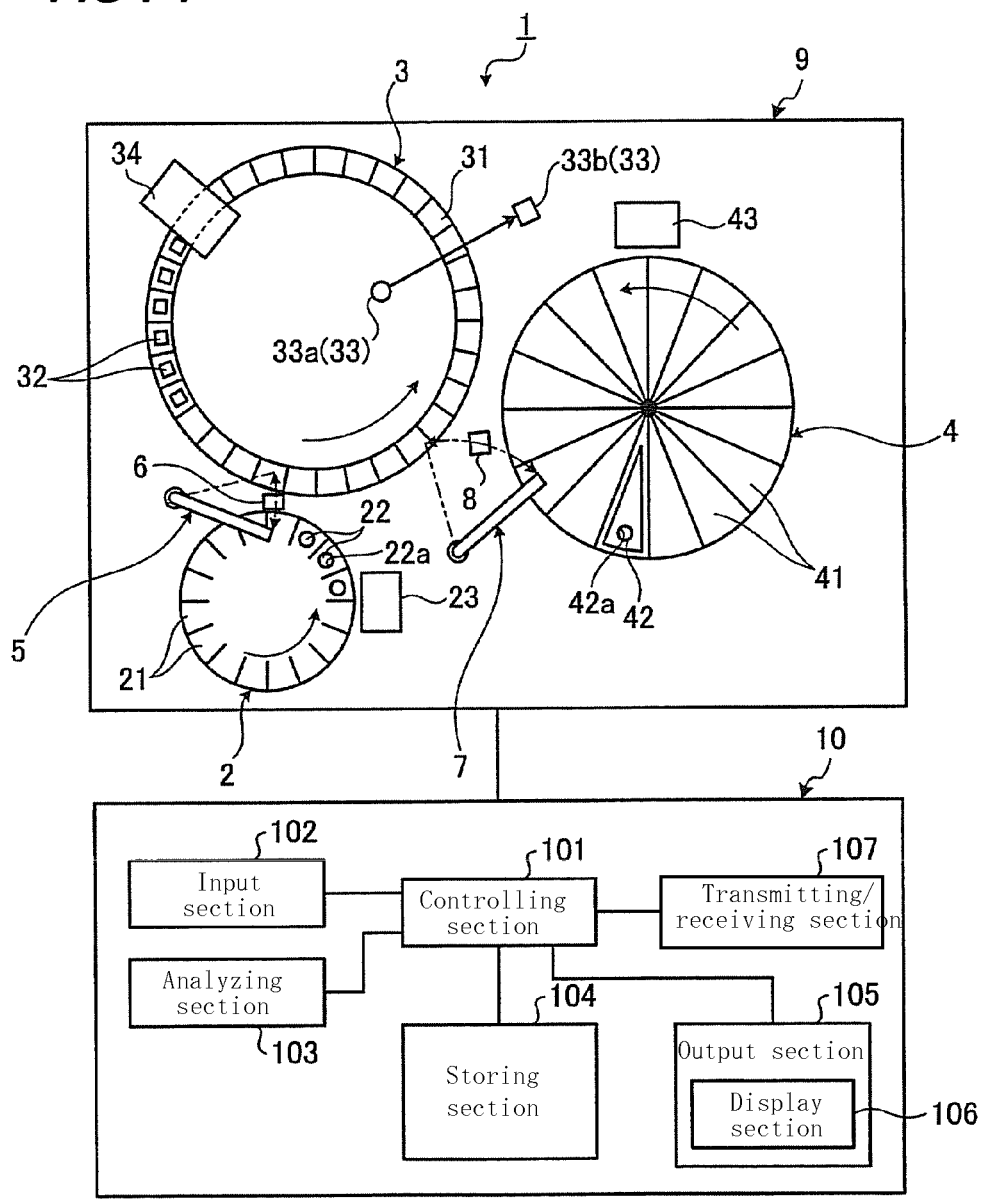
FIG. 1 is a schematic configuration diagram illustrating an automatic analyzer using a nozzle cleaning method of an embodiment of the present invention.

EXPLANATION OF SYMBOLS 1 automatic analyzer
2 sample table
21, 31, 41 receiving part
22 sample container
22a, 42a aperture
23, 43 reading section
3 reaction table
32 reaction container
33 photometer
33a light source
33b light receiving part
34 cleaning mechanism
4 reagent table
42 reagent container
5 sample dispensing mechanism
7 reagent dispensing mechanism
50 dispensing nozzle
51 arm
52 shaft
53 nozzle transferring section
54a, 54b tube
55 syringe
55a cylinder
55b plunger
56 plunger driving section
57 tank
58 electromagnetic valve
59 pump
6, 8 nozzle cleaning mechanism
60 cleaning tank
60a aperture
61 means for supplying cleaning liquid to be ejected
61a nozzle section
61b, 62b, 63b, 64a tube
61c tank
61d, 62d, 63c electromagnetic valve
61e pump
62 storage tank
62a aperture
62c waste tank 63 means for supplying cleaning liquid to be stored
63a nozzle section
64 overflow tank
9 measuring mechanism
10 controlling mechanism
101 controlling section
102 input section
103 analyzing section
104 storing section
105 output section
106 display section
107 transmitting/receiving section
L1 liquid for preload
L2 cleaning liquid
O vertical axis
S center line

BEST MODE FOR CARRYING OUT THE INVENTION

Hereinafter, with reference to the attached drawings, preferred embodiments of a nozzle cleaning method and a nozzle cleaning device of the present invention will be described in detail. It should be noted that the invention is not limited by such embodiments. It should also be noted that corresponding parts of the figures are given the same reference numerals in the description of the drawings.

Embodiment 1

FIG. 1 is a schematic configuration diagram illustrating an automatic analyzer using a nozzle cleaning method of an embodiment of the present invention. As shown in FIG. 1, an automatic analyzer 1 includes a measuring mechanism 9 for measuring light passing a reactant between a sample and a reagent, and a controlling mechanism 10 for controlling the overall automatic analyzer 1 including the measuring mechanism 9 and analyzing measurement results in the measuring mechanism 9. The automatic analyzer 1 automatically analyzes a plurality of samples by cooperation of these two mechanisms.

First, the measuring mechanism 9 is explained. The measuring mechanism 9 includes, broadly divided, a sample table 2, a reaction table 3, a reagent table 4, a sample dispensing mechanism (sample dispensing device) 5, a reagent dispensing mechanism (reagent dispensing device) 7, and nozzle cleaning mechanisms (nozzle cleaning devices) 6 and 8.

The sample table 2 has a disk-shape table, and includes a plurality of receiving parts 21 disposed at regular intervals along a circumferential direction of the table. In each receiving part 21, a sample container 22 containing a sample is removably received. The sample container 22 has an aperture 22a opening upwardly. The sample table 2 is rotated by a sample table driving section (not shown) in a direction shown in FIG. 1 by an arrow so that a vertical line passing the center of the sample table 2 is an axis of rotation. When the sample table 2 is rotated, the sample container 22 is delivered to a sample suctioning position where the sample is suctioned by the sample dispensing mechanism 5.

To the sample container 22, an identification label (not shown) having sample information related to the type and analysis items of the sample contained therein is attached. Meanwhile, the sample table 2 includes a reading section 23 for reading the information of the identification label of the sample container 22.

The reaction table 3 has a ring-shaped table, and includes a plurality of receiving parts 31 disposed at regular intervals along a circumferential direction of the table. In each receiving part 31, a transparent reaction container 32 containing a sample and a reagent is removably received in the form in which the container is upwardly opened. Furthermore, the reaction table 3 is rotated by a reaction table driving section (not shown) in a direction shown by an arrow in FIG. 1 so that a vertical line passing the center of the reaction table 3 is an axis of rotation. When the reaction table 3 is rotated, the reaction container 32 is delivered to a sample discharging position where a sample is discharged by the sample dispensing mechanism 5, or delivered to a reagent discharging position where a reagent is discharged by the reagent dispensing mechanism 7.

The reaction table 3 also includes a photometer 33. The photometer 33 has a light source 33a and a light receiving part 33b. The light source 33a emits analysis light of a predetermined wavelength. The light receiving part 33b measures a light flux which has been emitted from the light source 33a and has transmitted a reaction liquid resulting from reaction between the sample contained in the reaction container 32 and a reagent. In the photometer 33, the light source 33a and the light receiving part 33b are disposed at radially opposite positions across the receiving parts 31 of the reaction table 3. The reaction table 3 includes a cleaning mechanism 34 for exhausting the reaction liquid after the measurement from the reaction container 32 and cleaning the reaction container 32.

The reagent table 4 has a disk-shaped table, and includes a plurality of receiving parts 41 disposed at regular intervals along a circumferential direction of the table. In each receiving part 41, a reagent container 42 containing a reagent is removably received. The reagent container 42 has an aperture 42a opening upwardly. The reagent table 4 is rotated by a reagent table driving section (not shown) in a direction shown in FIG. 1 by an arrow so that a vertical line passing the center of the reagent table 4 is an axis of rotation. When the reagent table 4 is rotated, the reagent container 42 is delivered to a reagent suctioning position where the reagent is suctioned by the reagent dispensing mechanism 7.

To the reagent container 42, an identification label (not shown) having reagent information related to the type and contained amount of the reagent contained therein is attached. Meanwhile, the reagent table 4 includes a reading section 43 for reading the information of the identification label of the reagent container 42.

The sample dispensing mechanism 5 includes an arm, at the tip portion of which a dispensing nozzle for suctioning and discharging a sample is mounted and which freely rises/lowers in a vertical direction and rotates so that a vertical line passing its own base end portion is a central axis. The sample dispensing mechanism 5 is disposed between the sample table 2 and the reaction table 3. The sample dispensing mechanism 5 suctions the sample in the sample container 22 delivered by the sample table 2 to a predetermined position using the dispensing nozzle, rotates the arm, dispenses the sample into the reaction container 32 delivered by the reaction table 3 to a predetermined position to transfer the sample into the reaction container 32 on the reaction table 3 at a predetermined timing.

The reagent dispensing mechanism 7 includes an arm, at the tip portion of which a dispensing nozzle for suctioning and discharging a reagent is mounted and which freely rises/lowers in a vertical direction and rotates so that a vertical line passing its own base end portion is a central axis. The reagent dispensing mechanism 7 is disposed between the reagent table 4 and the reaction table 3. The reagent dispensing mechanism 7 suctions the reagent in the reagent container 42 delivered by the reagent table 4 to a predetermined position using the dispensing nozzle, rotates the arm, dispenses the reagent into the reaction container 32 delivered by the reaction table 3 to a predetermined position to transfer the reagent into the reaction container 32 on the reaction table 3 at a predetermined timing.

Figure 2:
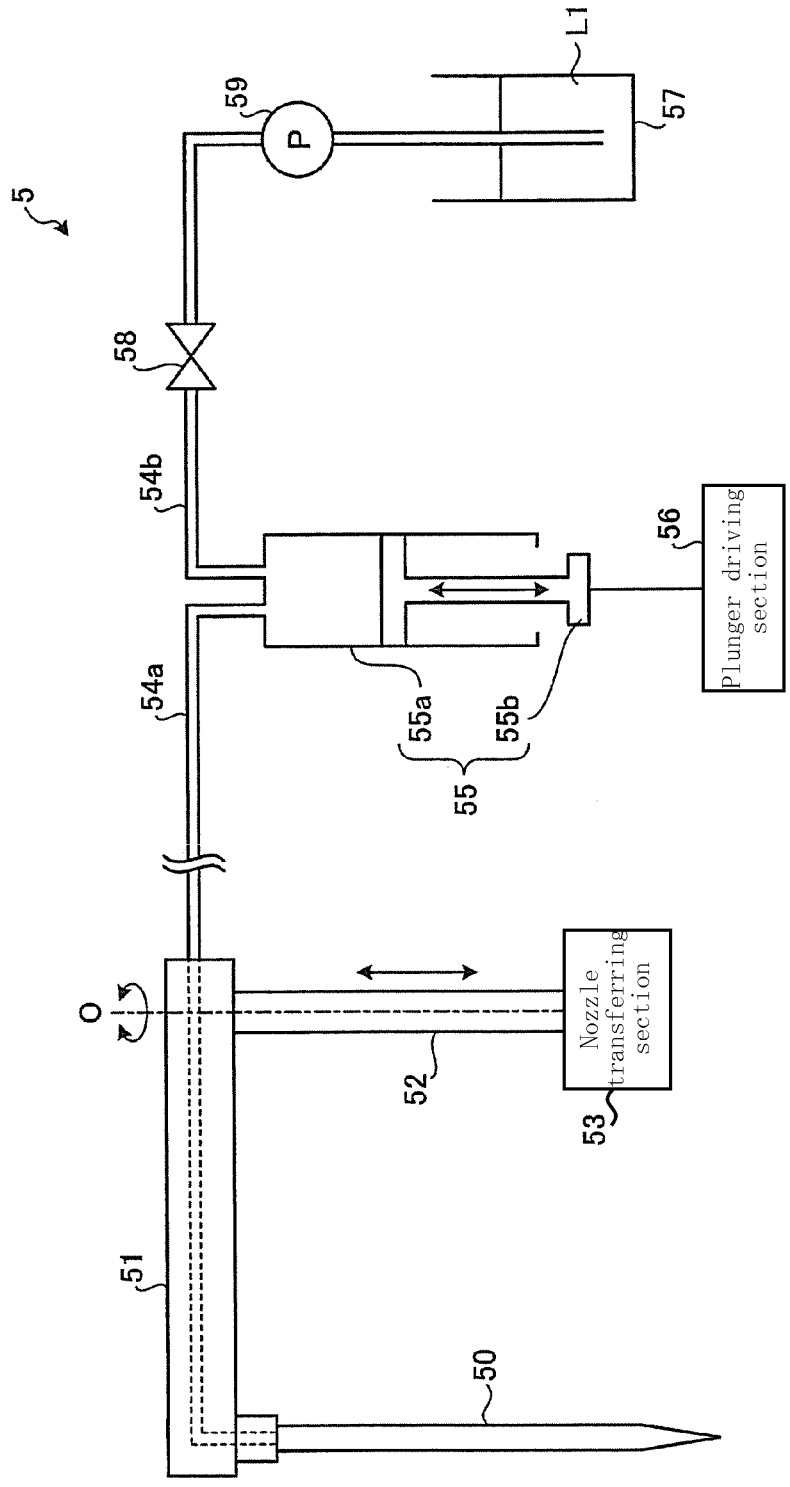
FIG. 2 is a schematic configuration diagram illustrating a dispensing device.

FIG. 2 shows a schematic configuration diagram of the sample dispensing mechanism 5 (same as the reagent dispensing mechanism 7). The sample dispensing mechanism 5 has a dispensing nozzle 50, as shown in FIG. 2. The dispensing nozzle 50 is made of stainless steel or the like formed into a bar-tube shape, and a tip side of the dispensing nozzle 50 has a taper shape. The tip of the taper shape is faced downward, and the base end of the upper side is attached to the tip of the arm 51. The arm 51 is horizontally disposed, and the base end of the arm 51 is fixed to the upper end of the shaft 52. The shaft 52 is vertically disposed, and is rotated by the nozzle transferring section 53 so that the vertical axis O is the center. When the shaft 52 is rotated, the arm 51 rotates in a horizontal direction to move the dispensing nozzle 50 in a horizontal direction. The shaft 52 is raised/lowered by the nozzle transferring section 53 along the vertical axis O. When the shaft 52 is raised/lowered, the arm 51 is raised/lowered in a vertical direction and raises/lowers the dispensing nozzle 50 in a vertical (up and down) direction which is a longitudinal direction of the dispensing nozzle 50.

To the base end of the dispensing nozzle 50, one end of a tube 54a is connected. The other end of the tube 54a is connected to a syringe 55. The syringe 55 has a tubular cylinder 55a connected with the other end of the tube 54a and a plunger 55b provided on the inner wall surface of the cylinder 55a so as to be capable of moving forward/backward in the cylinder 55a while sliding. The plunger 55b is connected to the plunger driving section 56. The plunger driving section 56 is configured using a linear motor, for example, and moves the plunger 55b forward to/backward from the cylinder 55a. To the cylinder 55a of the syringe 55, one end of the tube 54b is connected. The other end of the tube 54b is connected to a tank 57 containing a liquid for preload L1. In the middle of the tube 54b, an electromagnetic valve 58 and a pump 59 are connected. As the liquid for preload L1, an incompressible fluid such as distilled water and deaerated water is applied. This liquid for preload L1 is also applied as a cleaning liquid for cleaning inside the dispensing nozzle 50.

The sample dispensing mechanism 5 drives the pump 59, and by opening the electromagnetic valve 58, the liquid for preload L1 contained in the tank 57 is filled in the cylinder 55a of the syringe 55 via the tube 54b. Furthermore, the liquid for preload L1 is filled to the tip of the dispensing nozzle 50 through the tube 54a from the cylinder 55a. In such a condition in which the liquid for preload L1 is filled to the tip of the dispensing nozzle 50, the electromagnetic valve 58 is opened, and the pump 59 is stopped. In a case of suctioning a sample or a reagent, the plunger driving section 56 is driven to move the plunger 55b backward from the cylinder 55a, so that suctioning pressure is applied to the tip portion of the dispensing nozzle 50 via the liquid for preload L1 and the sample or reagent is suctioned by this suctioning pressure. On the other hand, in a case of discharging a sample or a reagent, the plunger driving section 56 is driven to move the plunger 55b forward to the cylinder 55a, so that discharging pressure is applied to the tip portion of the dispensing nozzle 50 via the liquid for preload L1 and the sample or reagent is discharged by this discharging pressure.

Although not shown in the figure, the sample dispensing mechanism 5 includes a liquid level sensing function to sense a liquid level of the sample and reagent dispensed by the dispensing nozzle 50. The liquid level sensing function includes, for example, a function to sense a liquid level based on change in electrostatic capacitance when the dispensing nozzle 50 contacts the sample or specimen.

Figure 3:
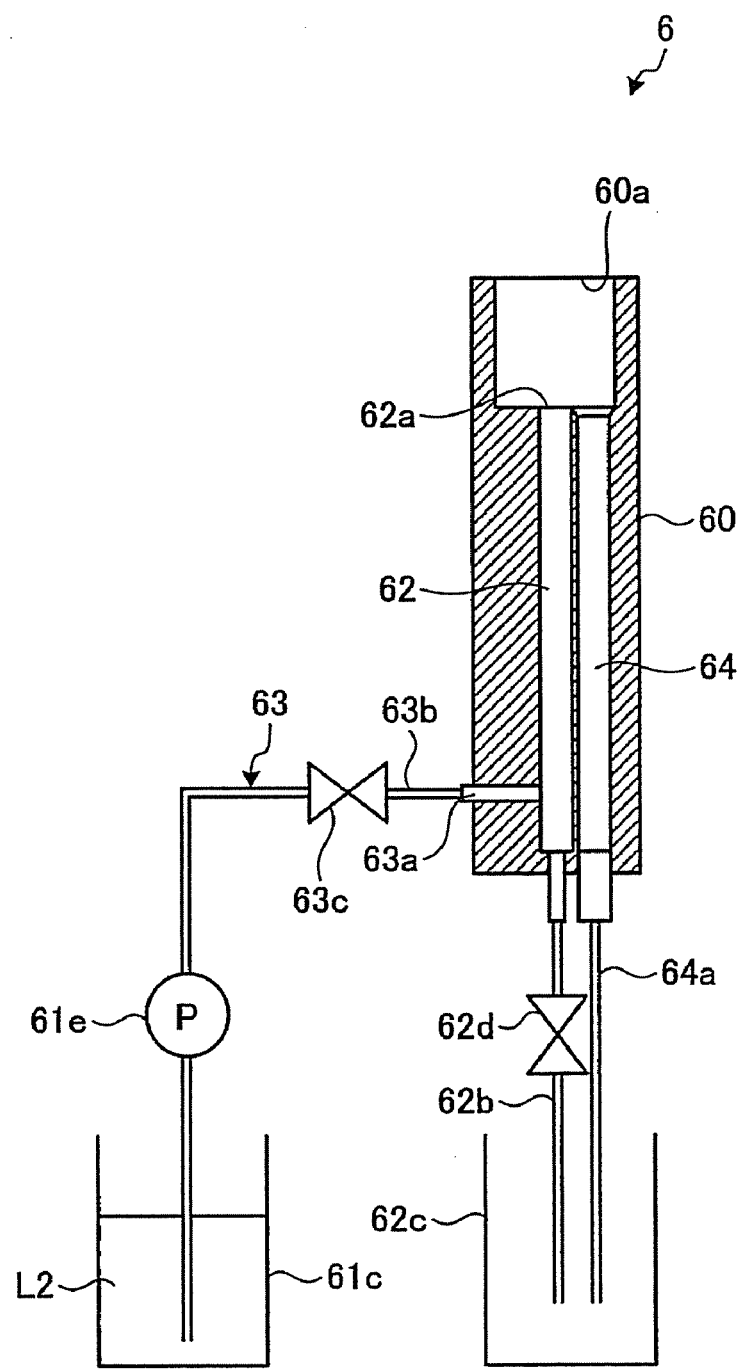
FIG. 3 is a schematic configuration diagram illustrating a nozzle cleaning device using a nozzle cleaning method of an embodiment 1 of the present invention.

The nozzle cleaning mechanism 6 is provided at a position between the sample table 2 and the reaction table 3 and in the middle of a track of horizontal movement of the dispensing nozzle 50 in the sample dispensing mechanism 5. The nozzle cleaning mechanism 8 is provided at a position between the reagent table 4 and the reaction table 3 and in the middle of a track of horizontal movement of the dispensing nozzle 50 in the reagent dispensing mechanism 7. FIG. 3 shows a schematic configuration diagram of the nozzle cleaning mechanism. As shown in FIG. 3, the nozzle cleaning mechanism 6 (same as the nozzle cleaning mechanism 8) has a cleaning tank 60. The cleaning tank 60 is formed in a tubular shape, and has an aperture 60a in the upper portion thereof so that the tip of the dispensing nozzle 50 lowering is inserted from the upper side.

In the center region of the cleaning tank 60, a rectangular or cylindrical storage tank 62 is provided. The storage tank 62 has an aperture 62a in the upper portion thereof so that the tip of the dispensing nozzle 50 lowering is inserted from the upper side. In the lower portion of the side surface of the storage tank 62, a means for supplying cleaning liquid to be stored 63 is provided. The means for supplying cleaning liquid to be stored 63 is connected to the storage tank 62 via the nozzle section 63a which is provided so that the discharging outlet thereof is faced inward of the storage tank 62. To the nozzle section 63a, one end of a tube 63b is connected, and the other end of the tube 63b is connected to a tank 61c containing a cleaning liquid L2. In the middle of the tube 63b, an electromagnetic valve 63c and a pump 61e are connected, and the tube 63b is connected from the nozzle section 63a to a tank 61c via the electromagnetic valve 63c and the pump 61e. As the cleaning liquid L2, distilled water, deaerated water or the like is applied. On the bottom portion of the storage tank 62, one end of the tube 62b is connected, and the other end of the tube 62b is connected to a waste tank 62c via the electromagnetic valve 62d.

In the cleaning tank 60, an overflow tank 64 is provided. The overflow tank 64 is disposed alongside with the storage tank 62 inside the cleaning tank 60. The aperture of the overflow tank 64 is formed in a mortar shape so as to form a slope which inclines downward from the aperture 62a of the storage tank 62, and the lower portion of the aperture is formed penetrating the bottom portion of the cleaning tank 60. To the lower portion of the overflow tank 64, one end of the tube 64a is connected. The other end of the tube 64a is connected to the waste tank 62c.

The nozzle cleaning mechanism 6 opens the electromagnetic valve 63c an drives the pump 61e, so that the cleaning liquid L2 contained in the tank 61c is supplied from the discharging outlet of the nozzle section 63a to the inside of the storage tank 62 via the tube 63b, and stored inside the storage tank 62. The cleaning liquid L2 which is supplied from the nozzle section 63a to the inside of the storage tank 62 and overflows from the aperture 62a is led from the cleaning tank 62 to the overflow tank 64 along the slope formed between the storage tank 62 and the overflow tank 64, and is exhausted from this overflow tank 64 to the waste tank 62c outside the cleaning tank 60 via the tube 64a. By opening the electromagnetic valve 62d, the cleaning liquid L2 stored in the storage tank 62 is exhausted to the waste tank 62c via the tube 62b.

In the automatic analyzer 1 having such a configuration, the sample dispensing mechanism 5 dispenses a sample from the sample container 22 to the reaction container 32. Furthermore, in the reaction container 32, the reagent dispensing mechanism 7 dispenses a reagent from the reagent container 42. While the reaction container 32 in which the sample and reagent have been dispensed is delivered by the reaction table 3 along a circumferential direction, the sample and the reagent are stirred and react, and the reaction container 32 passes between the light source 33a and the light receiving part 33b. Then, an analysis light emitted from the light source 33a and passing a reaction liquid in the reaction container 32 is measured by the light receiving part 33b, and concentration of a component or the like is analyzed. After termination of analysis, the reaction container 32 is cleaned by the cleaning mechanism 34 after exhausting the reaction liquid after measurement, and is subsequently used again in analysis of sample.

Next, the controlling mechanism 10 is explained. As shown in FIG. 1, the controlling mechanism 10 includes a controlling section 101, an input section 102, an analyzing section 103, a storing section 104, an output section 105 and a transmitting/receiving section 107. Each section included in the controlling mechanism 10 is electrically connected to the controlling section 101. The analyzing section 103 is connected to a photometer 33 via the controlling section 101, analyzes concentration of components of a sample or the like based on a light quantity received by the light receiving part 33b, and outputs the results of analysis to the controlling section 101. The input section 102 is a section for performing an operation of inputting items to be checked or the like to the controlling section 101, and for example, a keyboard, mouse or the like is used as an input section.

The storing section 104 is configured using a hard disk for magnetically storing information and a memory for electrically storing various programs related to a processing loaded by the automatic analyzer 1 from the hard disk in performing the processing, and stores information including results of analysis of a sample, and the like. The storing section 104 may include an auxiliary storage capable of reading information stored on a storage medium such as CD-ROM, DVD-ROM, PC card or the like.

The output section 105 is configured using a printer, speaker or the like, and under the control of the controlling section 101, outputs information related to analysis. The output section 105 includes a display section 106 configured using a display or the like. The display section 106 displays contents of analysis, alarm and the like, and a display panel or the like is used as the display section 106. The input section 102 and the display section 106 may be embodied by a touch panel. The transmitting/receiving section 107 has a function as an interface which transmits/receives information via a communication network not shown in accordance with a predetermined format.

Furthermore, to the controlling section 101, the nozzle transferring section 53, the plunger driving section 56, the electromagnetic valve 58 and the pump 59 of the aforementioned sample dispensing mechanism 5 (same as the reagent dispensing mechanism 7) are connected, and the pump 61e, the electromagnetic valves 63c and 62d of the aforementioned nozzle cleaning mechanism 6 (same as the nozzle cleaning mechanism 8) are also connected. The controlling mechanism 10 controls operation and processing of the sample dispensing mechanism 5, the reagent dispensing mechanism 7, the nozzle cleaning mechanisms 6 and 8 using various programs related to each processing of the automatic analyzer 1.

In the automatic analyzer 1 thus configured, the reagent dispensing mechanism 7 dispenses a reagent from the reagent container 42 to a plurality of reaction containers 32 delivered by the rotating reaction table 3 along a circumferential direction. The reaction containers 32 in which a reagent has been dispensed are delivered by the reaction table 3 along a circumferential direction, and a sample is dispensed by the sample dispensing mechanism 5 from the sample container 22 held on the sample table 2. After dispensing the reagent and the sample, the dispensing nozzle is cleaned by the nozzle cleaning mechanisms 6 and 8 before dispensing the next reagent and sample in order to prevent carry-over.

Figure 4:
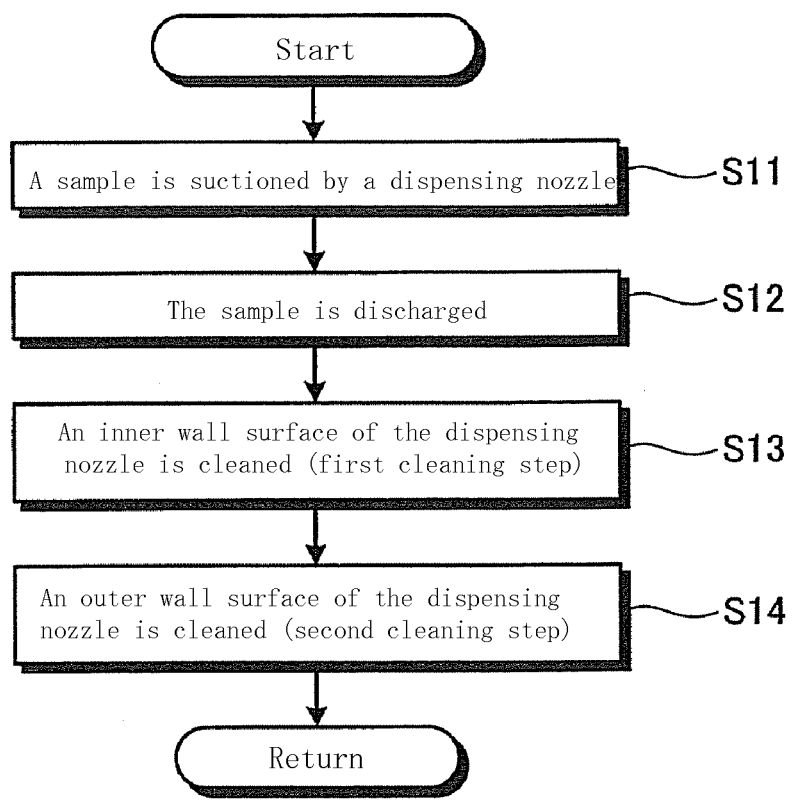
FIG. 4 is a flowchart of a nozzle cleaning operation of the embodiment 1 of the present invention.
Figure 5:
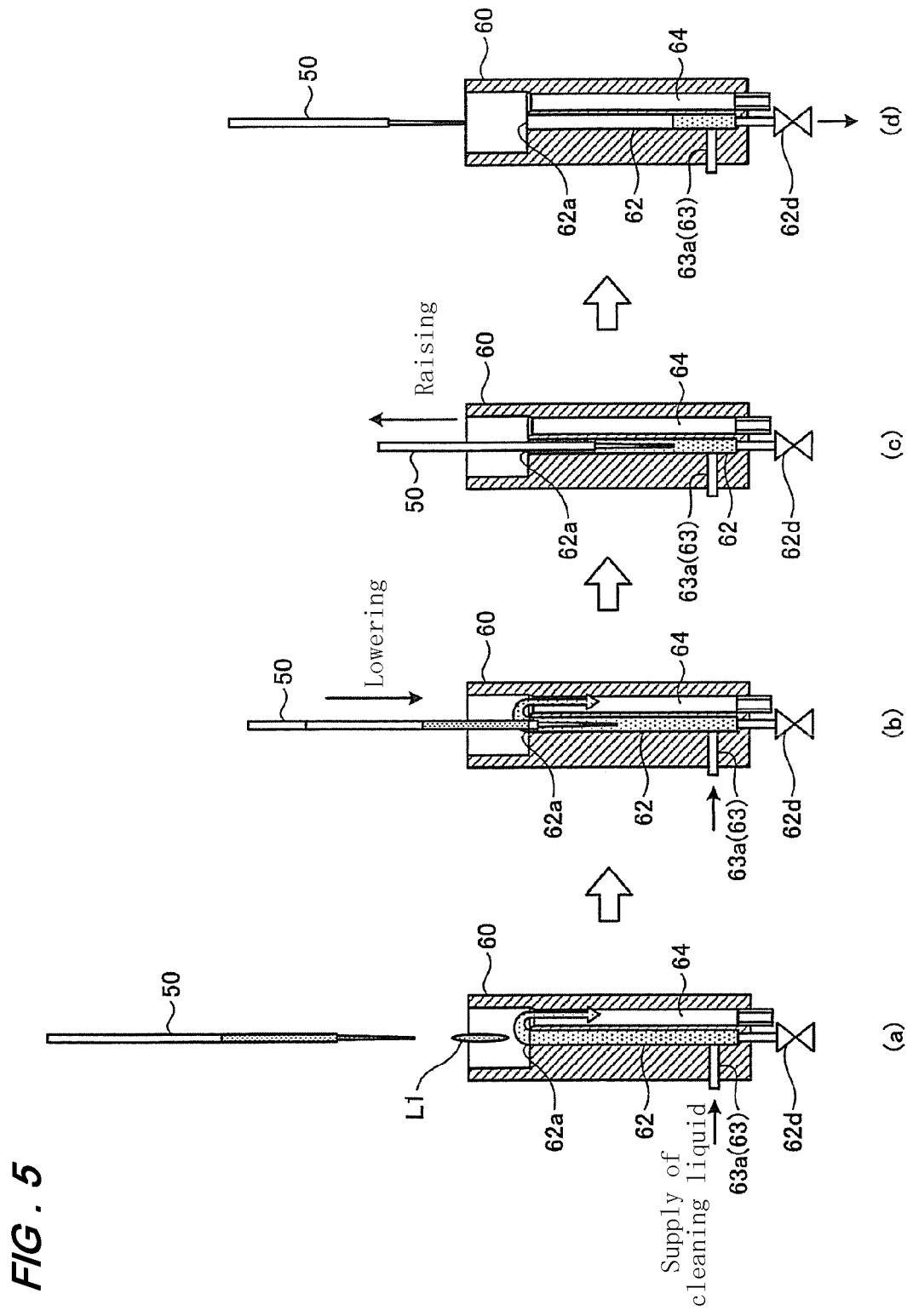
FIG. 5 is a diagram of operation illustrating the cleaning operation in the nozzle cleaning method of the embodiment 1 of the present invention.

Next, the nozzle cleaning mechanism 6 (same as the nozzle cleaning mechanism 8) shown in FIGS. 1 and 3 is explained in detail. FIG. 4 is a flowchart illustrating an operation of cleaning the dispensing nozzle, and FIG. 5 is a diagram of operation illustrating the cleaning operation of the nozzle cleaning mechanism.

As shown in FIG. 4, first, the controlling section 101 moves the dispensing nozzle 50 to above the aperture 22a of the sample container 22 at the sample suctioning position, and suctions the sample using the dispensing nozzle 50 (step S11). Next, the controlling section 101 moves the dispensing nozzle 50 to above the reaction container 32 at a sample discharging position, and discharges the sample (step S12). Thereafter, the controlling section 101 moves the dispensing nozzle 50 to above the aperture 62a of the storage tank 62 in the cleaning tank 60 in the nozzle cleaning mechanism 6, and above the storage tank 62 overflowed with the cleaning liquid L2 supplied by the means for supplying cleaning liquid to be stored 63, performs a first cleaning step (step S13) in which an inner wall surface of the dispensing nozzle 50 with the sample remaining inside thereof is cleaned by discharging the liquid for preload L1. Thereafter, the controlling section 101 performs a second cleaning step (step S14) in which the dispensing nozzle 50 is lowered and immersed into the storage tank 62 overflowed with the cleaning liquid L2 to clean at least the outer wall surface.

In the first cleaning step (step S13), as shown in FIG. 5(a), first, the controlling section 101 supplies the cleaning liquid L2 by the means for supplying cleaning liquid to be stored 63 connected to the lower portion of the side surface of the storage tank 62. On the storage tank 62 overflowed with the cleaning liquid L2 from the aperture 62a, the controlling section 101 drives the plunger driving section 56 to move the plunger 55b forward the cylinder 55a, so that the liquid for preload L1 is discharged together with the sample remaining in the dispensing nozzle 50. As a result of discharging the liquid for preload L1, the sample is removed from the inside of the dispensing nozzle 50, and the inner wall surface is cleaned. When the liquid for preload L1 discharged from the dispensing nozzle 50 and containing the sample reaches the storage tank 62, the cleaning liquid L2 supplied by the means for supplying cleaning liquid to be stored 63 is overflowed from the aperture 62a into the overflow tank 64 adjacent to the storage tank 62. Thus, the liquid for preload L1 containing the sample is forcibly exhausted to the overflow tank 64 together with the cleaning liquid L2 overflowed. As a result of overflowing the cleaning liquid L2 of the storage tank 62 when the liquid for preload L1 containing the sample falls and reaches the storage tank 62, the sample does not mix in the cleaning liquid L2 in the storage tank 62, which allows cleaning with clear cleaning liquid L2. Thus, it is possible to reduce the time of cleaning the outer wall surface of the dispensing nozzle 50 after the first cleaning step in comparison with the case of cleaning with a cleaning liquid L2 in which the sample has mixed in. The cleaning liquid L2 overflowed from the storage tank 62 is led to the overflow tank 64 along the slope formed between the storage tank 62 and the overflow tank 64 and is discarded in the waste tank 62c via the tube 64a connected to the overflow tank 64.

After termination of the first cleaning step, the procedure goes to the second cleaning step (step S14). As shown in FIG. 5(b), the controlling section 101 lowers and immerses the dispensing nozzle 50 with the sample remaining on the outer wall surface on the storage tank 62 overflowed with the cleaning liquid L2 supplied by the means for supplying cleaning liquid to be stored 63 which is connected in the lower portion of the side surface of the storage tank 62 via the nozzle section 63a, using the nozzle transferring section 53. When the tip of the dispensing nozzle 50 with the sample attached on the outer wall surface is lowered and immersed into the cleaning liquid L2 in the storage tank 62, in the aperture 62a of the storage tank 62, the cleaning liquid L2 supplied by the means for supplying cleaning liquid to be stored 63 to the storage tank 62 overflows into the overflow tank 64. Thus, the sample cleaned from the outer wall surface of the dispensing nozzle 50 by lowering and immersing the dispensing nozzle 50 into the cleaning liquid L2 is forcibly overflowed to the overflow tank 64 together with the cleaning liquid L2 immediately after cleaning from the dispensing nozzle 50. Since a wall surface between the storage tank 62 and the overflow tank 64 has a shape forming a slope which inclines downwardly from the storage tank 62 to the overflow tank 64, overflow is readily performed. Furthermore, by adjusting the speed of lowering the dispensing nozzle 50 and the amount of cleaning liquid L2 to be overflowed, it is possible to overflow the sample attached to the dispensing nozzle 50 together with the cleaning liquid L2 after cleaning with the cleaning liquid L2 in the storage tank 62, without diffusing. Since the cleaning liquid L2 containing the removed sample is exhausted without remaining in the storage tank 62, clear cleaning liquid L2 is stored in the storage tank 62, and the contaminated cleaning liquid L2 does not attach again to the dispensing nozzle 50, thereby allowing a reduced cleaning time.

In the nozzle cleaning method of the present invention, it may be designed so that cleaning of the outer wall surface is terminated within a time required for lowering the dispensing nozzle 50 into the storage tank 62. Furthermore, after termination of lowering the dispensing nozzle 50, the dispensing nozzle 50 may be kept immersed in the storage tank 62 to further clean the outer wall surface. The cleaning liquid L2 overflowed from the storage tank 62 is led to the overflow tank 64, and is discarded in the waste tank 62c via the tube 64a connected to the overflow tank 64.

Here, the depth of insertion of the dispensing nozzle 50 in the storage tank 62 may be any depth equal to or greater than the depth of burying the dispensing nozzle 50 in the sample or the like at the time of suctioning the sample or reagent, and is selected and determined based on analytical information. The analytical information is stored in the storing section 104 in association with the sample container 22 placed on the sample table 2. The depth of burying the dispensing nozzle 50 at the time of suctioning a serum sample or reagent is about several millimeters (for example, 3 mm) and that at the time of suctioning a whole blood sample is a depth depending on the total depth of the sample (for example, 70% of the total depth from liquid level). Thus, the depth of insertion of the dispensing nozzle 50 in the storage tank 62 is set depending on the type of sample, so that the dispensing nozzle 50 is inserted in the storage tank 62 at a depth equal to or greater than the depth of burying the dispensing nozzle 50 at the time of suctioning. Even in a case of nozzle cleaning after suctioning a whole blood sample in which depth of burying is the maximum, the position of the tip of the dispensing nozzle 50 at the time of inserting the dispensing nozzle 50 in the storage tank 62 is above the portion connecting the nozzle section 63a from the means for supplying cleaning liquid to be stored 63. By positioning the tip portion of the dispensing nozzle 50 higher than the nozzle section 63a, even in a case in which the sample remains on the outer wall surface of the dispensing nozzle 50, the inside of the storage tank 62 can be maintained clean by supplying the cleaning liquid L2 from the means for supplying cleaning liquid to be stored 63.

After termination of cleaning the outer wall surface of the dispensing nozzle 50, supply of the cleaning liquid L2 from the means for supplying cleaning liquid to be stored 63 is stopped, and overflow of the cleaning liquid L2 of the storage tank 62 is also stopped. As described above, by frequently controlling the supply of the cleaning liquid L2 from the means for supplying cleaning liquid to be stored 63, it is possible to reduce an amount of cleaning liquid L2 to be discarded. After termination of overflow, as shown in FIG. 5(c), the dispensing nozzle 50 is raised by the nozzle transferring section 53, and is drawn up from the storage tank 62. By adjusting the speed of raising the dispensing nozzle 50, it is possible to reduce an amount of the cleaning liquid L2 attaching to the dispensing nozzle 50.

After drawing the dispensing nozzle 50 from the storage tank 62, as shown in FIG. 5(d), the cleaning liquid L2 stored in the storage section 62 by opening the electromagnetic valve 62d is exhausted to the waste tank 62c via the tube 62b.

Although a case has been described above in which only the outer wall surface of the dispensing nozzle 50 is cleaned in the second cleaning step, it is also possible to immerse and clean the dispensing nozzle 50 in the storage tank 62 to clean the outer wall surface while driving the plunger driving section 56 to move the plunger 55b backward from and forward to the cylinder 55a after lowering of the dispensing nozzle as shown in FIG. 5(b) and before raising of the dispensing nozzle 50 as shown in FIG. 5(c) so that the dispensing nozzle 50 suctions/discharges the cleaning liquid L2 in the storage tank 62 to further clean the inner wall surface of the dispensing nozzle 50.

Furthermore, although in the aforementioned embodiment overflow of the storage tank 62 is stopped before the raising of the dispensing nozzle 50 shown in FIG. 5(c), overflow may be continued by continuing supply of the cleaning liquid L2 from the means for supplying cleaning liquid to be stored 63.

Next, using FIG. 6, operation time of each step of the nozzle cleaning method of the present embodiment is explained. FIG. 6 is a timing diagram of cleaning operation of the nozzle cleaning mechanism using the present invention.

The dispensing nozzle 50 after discharging a sample or a reagent to the reaction container 32 received in the receiving part 31 of the reaction table 3 is transferred by the nozzle transferring section 53 to the upper portion of the storage tank 62 of the nozzle cleaning mechanism 6 or 8. After transferring the dispensing nozzle 50, as shown in FIG. 6(a), by driving the plunger driving section 56 to move the plunger 55b forward to the cylinder 55a, the liquid for preload L1 is discharged from the dispensing nozzle 50 together with the sample remaining in the dispensing nozzle 50 (t1). Then, as shown in FIG. 6(b), the storage tank 62 is controlled by the controlling section 101 so that, after the point t1 when the plunger driving section 56 is driven, by the point t2 when the liquid for preload L1 falls and reaches the storage tank 62 after driving the plunger driving section 56, the cleaning liquid L2 is supplied at least from the means for supplying cleaning liquid to be stored 63 and is overflowed from the aperture 62a of the storage tank 62 to the overflow tank 64 along the slope formed between the storage tank 62 and the overflow tank 64.

After cleaning the inner wall surface of the dispensing nozzle 50, the controlling section 101 stops driving of the plunger driving section 56 to stop discharging of the liquid for preload L1 (t3), and as a result, overflow of the storage tank 62 is also stopped after the discharged liquid for preload L1 reaches to the storage tank 62 (t4). While the liquid for preload L1 containing the sample is discharged from the dispensing nozzle 50 and is led to the storage tank 62, at least the storage tank 62 is controlled to be overflowed by supplying the cleaning liquid L2 from the means for supplying cleaning liquid to be stored 63. By such controlling, it is possible to prevent the sample from mixing in the cleaning liquid L2 in the storage tank 62.

Thereafter, as shown in FIG. 6(c), the dispensing nozzle 50 is lowered and immersed into the storage tank 62 by the nozzle transferring section 53 (t5). Then, as shown in FIG. 6(b), the storage tank 62 is controlled so that, after the point t5 when the nozzle transferring section 53 is driven, by the point t6 when the tip of the dispensing nozzle 50 is immersed in the cleaning liquid L2 in the storage tank 62, the cleaning liquid L2 is supplied at least from the means for supplying cleaning liquid to be stored 63 and overflowed in the aperture 62a of the storage tank 62.

At the time point of termination of lowering the dispensing nozzle 50 (t7), cleaning of the outer wall surface of the dispensing nozzle 50 is terminated, and the overflow of the storage tank 62 is also stopped (t8). In a case of cleaning the outer wall surface (or inner and outer wall surfaces) of the dispensing nozzle 50 in the storage tank 62 after termination of lowering the dispensing nozzle 50, overflow is stopped after termination of the immersion cleaning in the storage tank (in such a case, the interval between t7 and t8 becomes longer by the time of immersion cleaning).

Thereafter, as shown in FIG. 6(c), the dispensing nozzle 50 is started to be drawn up from the storage tank 62 by driving the nozzle transferring section 53 (t9), and the drawing of the dispensing nozzle 50 is completed at t11. The cleaning liquid L2 in the storage tank 62 is, as shown in FIG. 6(d), exhausted to the waste tank 62c by opening the electromagnetic valve 62d after the point t10 when the dispensing nozzle 50 is raised vertically by the nozzle transferring section 53 and drawn from the cleaning liquid L2 in the storage tank 62.

Use of the nozzle cleaning method of the present embodiment allows cleaning of a dispensing nozzle in a single storage tank to allow reduction in cleaning time, and also reduces carry-over of the sample into the storage tank to allow efficient cleaning. Furthermore, the cleaning tank of the present embodiment consists of a single storage tank and an overflow tank to which the cleaning liquid overflowed from the storage tank is exhausted, does not require providing extra equipment, such as a waste tank, and has an advantage that the cleaning mechanism is simplified, which results in reduction of costs.

As an example of variation of the present embodiment, by continuing supply of the cleaning liquid L2 from the means for supplying cleaning liquid to be stored 63 through the first cleaning step and the second cleaning step, the storage tank 62 may be continued to overflow always. In such a case, exhaustion of the cleaning liquid L2 stored in the storage tank 62 to the waste tank 62c shown in FIG. 5(d) is omitted, and cleaning of the dispensing nozzle 50 is subsequently performed.

Furthermore, as an example of variation of the present embodiment, it is also possible to supply the cleaning liquid L2 from the means for supplying cleaning liquid to be stored 63 to overflow the storage tank 62 through the first cleaning step and the second cleaning step, stop supply of the cleaning liquid L2 from the means for supplying cleaning liquid to be stored 63 before the raising of the dispensing nozzle 50 shown in FIG. 5(c), and draw up the dispensing nozzle 50 from the storage tank 62 by the nozzle transferring section 53. Thereafter, the cleaning liquid L2 in the storage tank 62 shown in FIG. 5(d) is exhausted in the waste tank 62c, and cleaning of the dispensing nozzle 50 is newly performed. The present method is preferred since it allows a reduced amount of the cleaning liquid L2 to be used, while maintaining a higher degree of clarity of the cleaning liquid L2 in the storage tank 62.

Embodiment 2

Next, the embodiment 2 of the nozzle cleaning method of the present invention is explained. The embodiment 2 is different from the embodiment 1 in that in the embodiment 2 a means for supplying cleaning liquid to be ejected 61 is disposed above the storage tank 62 and the overflow tank 64 in the cleaning tank 60.

Figure 7:
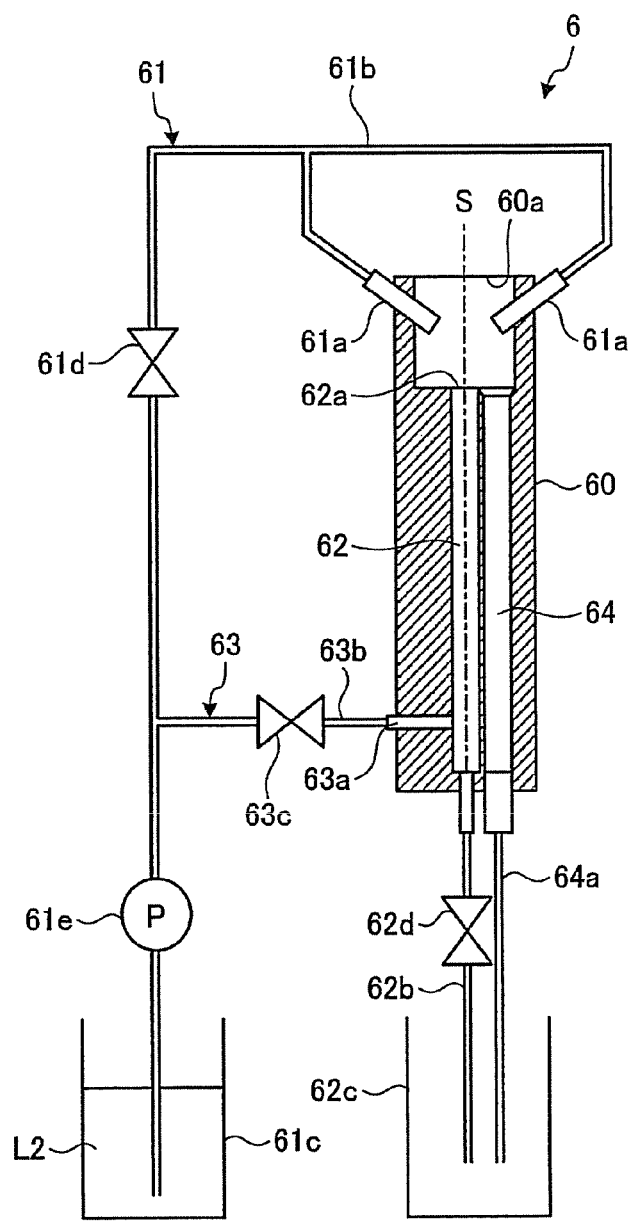
FIG. 7 is a schematic configuration diagram illustrating a nozzle cleaning device using a nozzle cleaning method of an embodiment 2 of the present invention.
Figure 8:
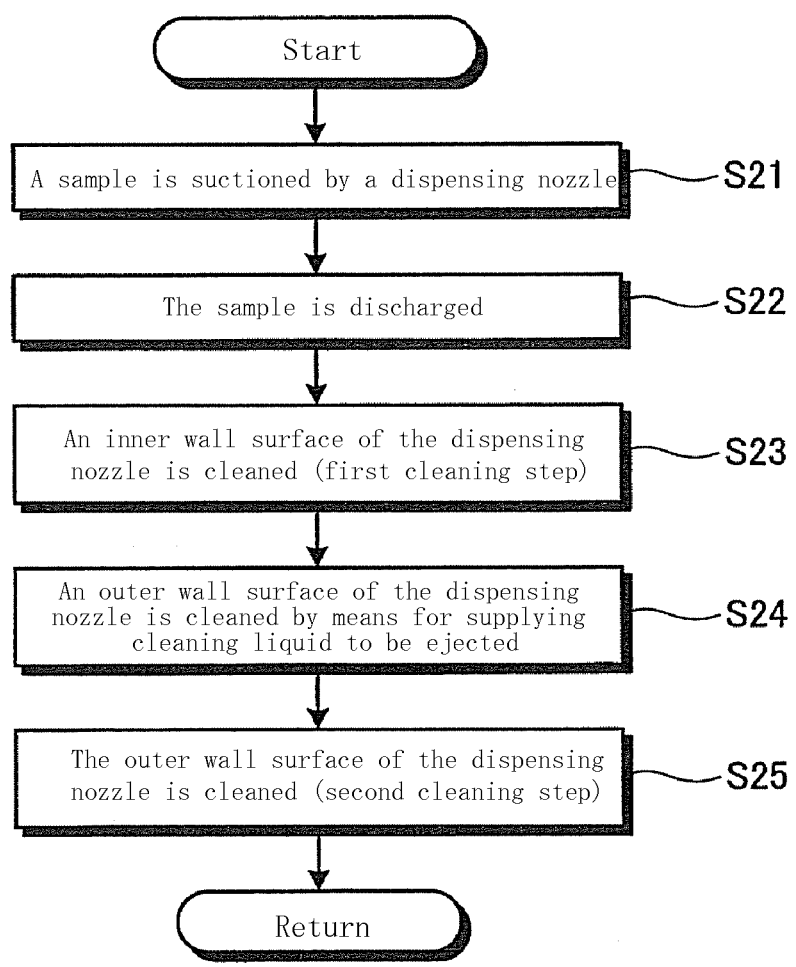
FIG. 8 is a flowchart of the nozzle cleaning operation of the embodiment 2 of the present invention.
Figure 9:
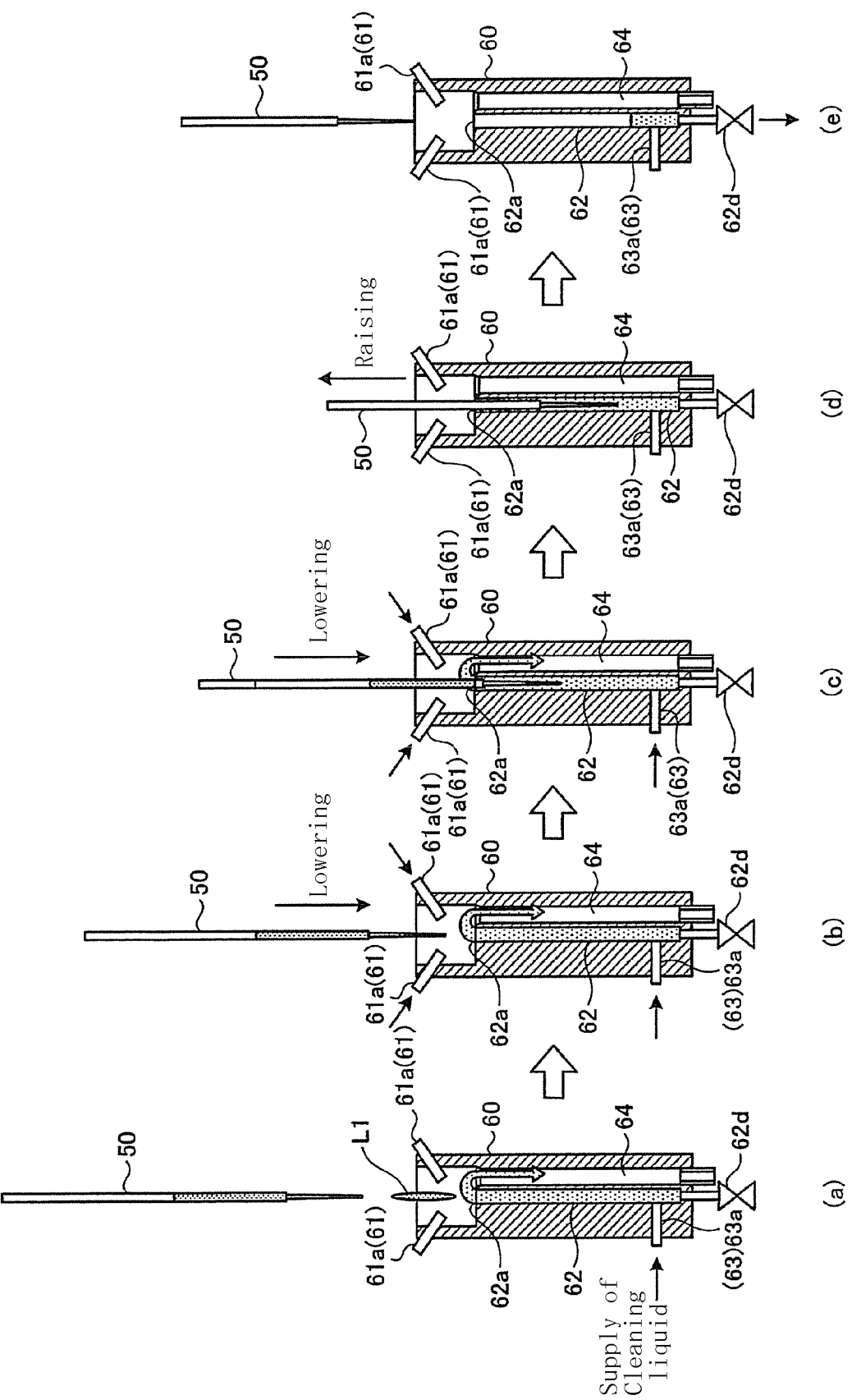
FIG. 9 is a diagram of operation illustrating the cleaning operation in the nozzle cleaning method of the embodiment 2 of the present invention.

FIG. 7 shows a schematic configuration diagram of a nozzle cleaning device of the present embodiment, FIG. 8 shows a flowchart illustrating the cleaning operation, and FIG. 9 shows a diagram of operation illustrating the cleaning operation.

As shown in FIG. 7, in the cleaning tank 60 of the nozzle cleaning device of the present embodiment, a means for supplying cleaning liquid to be ejected 61 is provided. The means for supplying cleaning liquid to be ejected 61 has a nozzle section 61a. A plurality of (two in the present embodiment) nozzle sections 61a are disposed in an upper portion in the cleaning tank 60 toward a vertical center line S of the cleaning tank 60, so that the discharging outlet faces obliquely downward. To each nozzle section 61a, one branched end of the tube 61b is connected. Furthermore, the tube 61b is formed so as to join together during when it extends from one end to the other end. The other end of the tube 61b is connected to a tank 61c containing a cleaning liquid L2. Furthermore, in the middle of the tube 61b joined together, an electromagnetic valve 61d and a pump 61e are connected.

The aspects that a storage tank 62 and an overflow tank 64 are provided inside the cleaning tank 60 in the lower region of the nozzle section 61a and a tube 62b and an electromagnetic valve 62d are disposed in the bottom portion of the storage tank 62 and that a means for supplying cleaning liquid to be stored 63 is provided in the lower portion of the side surface of the storage tank 62 are the same as in the embodiment 1.

In the present embodiment, by opening the electromagnetic valve 61d and driving the pump 61e, the cleaning liquid L2 contained in the tank 61c is ejected from the discharging outlet of the nozzle section 61a to the inside of the cleaning tank 60 via the tube 61b. Furthermore, by opening the electromagnetic valve 63c and driving the pump 61e, the cleaning liquid L2 contained in the tank 61c is supplied from the discharging outlet of the nozzle section 63a to the inside of the storage tank 62 via the tube 63b, and is stored inside the storage tank 62. The cleaning liquid L2 discharged from the nozzle section 61a to the inside of the cleaning tank 60 and the cleaning liquid L2 supplied from the nozzle section 63a to the inside of the storage tank 62 and overflowing from the aperture 62a of the storage tank 62 are overflowed into the overflow tank 64. Since a wall surface between the storage tank 62 and the overflow tank 64 has a shape forming a slope which inclines downwardly from the storage tank 62 to the overflow tank 64, the cleaning liquid L2 is led from the aperture 62a to the inside of the overflow tank 64 along the slope. The overflowed cleaning liquid L2 and the like are exhausted from the overflow tank 64 to the waste tank 62c outside the cleaning tank 60 via the tube 64a. Furthermore, by opening the electromagnetic valve 62d, the cleaning liquid L2 stored in the storage section 62 is exhausted to the waste tank 62c via the tube 62b.

In the present embodiment, as shown in FIG. 8, steps S21, S22, S23 and S25 are the same steps as in the embodiment 1, but the present embodiment is different from the embodiment 1 in that a step is provided between the steps S23 and S25, in which the dispensing nozzle 50 is entered and lowered in a flow path where the cleaning liquid L2 has been ejected by the means for supplying cleaning liquid to be ejected 61 in the upper portion of the storage tank 62 overflowed with the cleaning liquid L2 and the outer wall surface of the dispensing nozzle 50 is cleaned (step S24). A sample is suctioned by the dispensing nozzle 50 (step S21), the sample is discharged into the reaction container 32 (step S22), the inner wall surface of the dispensing nozzle 50 is cleaned by discharging the liquid for preload L1 on the storage tank 62 which is supplied with the cleaning liquid L2 by the means for supplying cleaning liquid to be stored 63 and thereby overflowed with the cleaning liquid L2 (step S23), and the dispensing nozzle 50 is lowered and entered in a flow path where the cleaning liquid L2 has been ejected from the nozzle section 61a of the means for supplying cleaning liquid to be ejected 61 on the storage tank 62 overflowed with the cleaning liquid L2, and the outer surface wall is cleaned (step S24). Successively, the dispensing nozzle 50 is lowered and immersed into the storage tank 62 overflowed with the cleaning liquid L2 to further clean at least the outer wall surface (step S25).

In the first cleaning step (step S23), as shown in FIG. 9(a), first, the controlling section 101 supplies the cleaning liquid L2 by the means for supplying cleaning liquid to be stored 63 connected to the lower portion of the side surface of the storage tank 62. On the storage tank 62 overflowed with the cleaning liquid L2 via the aperture 62a, the controlling section 101 drives the plunger driving section 56 to move the plunger 55b toward the cylinder 55a, thereby discharging the liquid for preload L1 together with the sample remaining in the dispensing nozzle 50. As a result of discharging the liquid for preload L1, the sample is removed from the inside of the dispensing nozzle 50, and the inner wall surface thereof is cleaned. When the liquid for preload L1 discharged from the dispensing nozzle 50 and containing the sample reaches the storage tank 62, the cleaning liquid L2 supplied by the means for supplying cleaning liquid to be stored 63 is overflowed from the aperture 62a into the overflow tank 64 adjacent to the storage tank 62. Thus, the liquid for preload L1 containing the sample is forcibly exhausted into the overflow tank 64 together with the cleaning liquid L2 overflowed. As a result of overflowing the cleaning liquid L2 of the storage tank 62 when the liquid for preload L1 containing the sample falls and reaches the storage tank 62, the sample does not mix in the cleaning liquid L2 in the storage tank 62, which allows subsequent immersion cleaning with clear cleaning liquid L2. The cleaning liquid L2 overflowed from the storage tank 62 is led to the overflow tank 64, and is discarded into the waste tank 62c via the tube 64a connected to the overflow tank 64.

After termination of the first cleaning step, as shown in FIG. 9(b), the controlling section 101 lowers and enters the dispensing nozzle 50 in a flow path where the cleaning liquid L2 has been ejected from the nozzle section 61a of the means for supplying cleaning liquid to be ejected 61 in the upper portion of the storage tank 62 overflowed with the cleaning liquid L2 and cleans the outer wall surface of the dispensing nozzle 50. In FIG. 9(b), in a condition in which the cleaning liquid L2 is supplied from the nozzle section 63a of the means for supplying cleaning liquid to be stored 63 to the storage section 62 and the cleaning liquid L2 is overflowed from the aperture 62a of the storage tank 62 to the overflow tank 64, the dispensing nozzle 50 is lowered and entered so as to be inserted in the aperture 60a of the cleaning tank 60. As a result, the cleaning liquid L2 ejected from the nozzle section 61a collides the outer wall surface of the dispensing nozzle 50 along a longitudinal direction (entering direction) of the dispensing nozzle 50, and the sample attached to the outer wall surface of the dispensing nozzle 50 is removed, thereby cleaning the outer wall surface of the dispensing nozzle 50. The removed sample falls in the storage tank 62 together with the cleaning liquid L2. Since the storage tank 62 is overflowed with the cleaning liquid L2 from the aperture 62a, the removed sample is exhausted to the overflow tank 64 together with the cleaning liquid L2 overflowed.

Next, as shown in FIG. 9(c), while continuing to eject the cleaning liquid L2 from the nozzle section 61a in the storage tank 62 overflowed with the cleaning liquid L2 supplied by the means for supplying cleaning liquid to be stored 63, the dispensing nozzle 50 is lowered and immersed into the cleaning liquid L2 in the storage tank 62. When the dispensing nozzle 50 is immersed in the cleaning liquid L2 in the storage tank 62, the cleaning liquid L2 is continuously supplied by the means for supplying cleaning liquid to be stored 63 connected to the lower portion of the storage tank 62 via the nozzle section 63a. Thus, in the aperture 62a of the storage tank 62, the cleaning liquid L2 overflows to the overflow tank 64, and the sample removed by ejecting the cleaning liquid L2 from the nozzle section 61a and the sample cleaned from the outer wall surface by immersion in the cleaning liquid L2 in the storage tank 62 are forcibly overflowed to the overflow tank 64 together with the cleaning liquid L2.

After termination of cleaning the outer wall surface of the dispensing nozzle 50, supply of the cleaning liquid L2 from the means for supplying cleaning liquid to be stored 63 is stopped, and overflow of the cleaning liquid L2 of the storage tank 62 is also stopped. After termination of overflow, as shown in FIG. 9(d), the dispensing nozzle 50 is raised by the nozzle transferring section 53, and is drawn up from the storage tank 62.

After drawing the dispensing nozzle 50 from the storage tank 62, as shown in FIG. 9(e), the cleaning liquid L2 stored in the storage section 62 is exhausted to the waste tank 62c via the tube 62b by opening the electromagnetic valve 62d.

Figure 10:
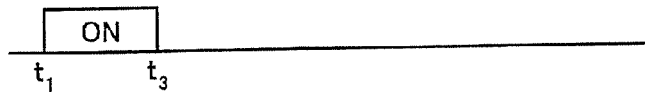
FIG. 10 is a timing diagram illustrating the cleaning operation in the nozzle cleaning method of the embodiment 2 of the present invention.
Figure 10:
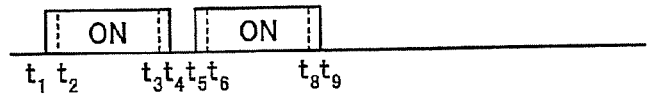
Figure 10:
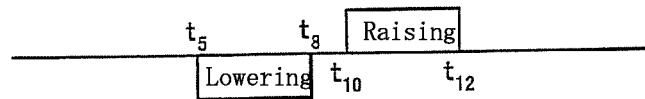
Figure 10:
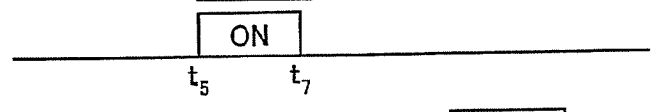
Figure 10:

Next, using FIG. 10, operation time of each step of the nozzle cleaning method of the present embodiment is explained. FIG. 10 is a timing diagram of the cleaning operation of the nozzle cleaning mechanism using the present embodiment.

The dispensing nozzle 50 after discharging a sample or a reagent into the reaction container 32 received in the receiving part 31 of the reaction table 3 is transferred by the nozzle transferring section 53 to the upper portion of the storage tank 62 of the nozzle cleaning mechanism 6 or 8. After transferring the dispensing nozzle 50, as shown in FIG. 10(a), by driving the plunger driving section 56 to move the plunger 55b forward to the cylinder 55a, the liquid for preload L1 is discharged from the dispensing nozzle 50 together with the sample remaining in the dispensing nozzle 50 (t1). Then, as shown in FIG. 10(b), the storage tank 62 is controlled by the controlling section 101 so that, after the point t1 when the plunger driving section 56 is driven, by the point t2 when the liquid for preload L1 falls and reaches the storage tank 62 after driving the plunger driving section 56, the cleaning liquid L2 is supplied at least from the means for supplying cleaning liquid to be stored 63 and is overflowed from the aperture 62*a* of the storage tank 62 to the overflow tank 64 along the slope formed between the storage tank 62 and the overflow tank 64.

After cleaning the inner wall surface of the dispensing nozzle 50, the controlling section 101 stops the plunger driving section 56 (t3), and as a result, overflow of the storage tank 62 is also stopped after the discharged liquid for preload L1 reaches the storage tank 62 (t4). While the liquid for preload L1 containing the sample is discharged from the dispensing nozzle 50 and is led to the storage tank 62, at least the storage tank 62 is controlled to be overflowed by supplying the cleaning liquid L2 from the means for supplying cleaning liquid to be stored 63. By such controlling, it is possible to prevent the sample from mixing in the cleaning liquid L2 in the storage tank 62.

Thereafter, as shown in FIGS. 10(*c*) and 10(*d*), the dispensing nozzle 50 is lowered and entered by the nozzle transferring section 53 in a flow path where the cleaning liquid L2 is ejected by the means for supplying cleaning liquid to be ejected 61 in the upper portion of the cleaning tank 60 (t5). Then, as shown in FIGS. 10(*b*) to 10(*d*), the storage tank 62 is controlled so that, after the cleaning liquid L2 is ejected by the means for supplying cleaning liquid to be ejected 61 (t5), by the point t6 which is the time point when the cleaning liquid L2 collides the outer wall surface of the dispensing nozzle 50 to remove the sample attached to the dispensing nozzle 50 and the cleaning liquid L2 containing the sample falls and reaches the storage tank 62, the cleaning liquid L2 is supplied at least from the means for supplying cleaning liquid and is overflowed from the aperture 62*a* of the storage tank 62. The dispensing nozzle 50 is lowered and entered in a flow path where the cleaning liquid L2 is ejected from the nozzle section 61*a* and then lowered and immersed into the storage tank 62. While the dispensing nozzle 50 is lowered by the nozzle transferring section 53, at least the storage tank 62 is controlled to be overflowed by supplying the cleaning liquid L2 from the means for supplying cleaning liquid to be stored 63. After the uppermost portion of the sample remaining in the outer wall surface of the dispensing nozzle 50 is cleaned with the cleaning liquid L2 discharged from the nozzle section 61*a*, ejection of the cleaning liquid L2 by the means for supplying cleaning liquid to be ejected 61 is stopped (t7).

At the time point of termination of lowering the dispensing nozzle 50 (t8), cleaning of the outer wall surface of the dispensing nozzle 50 is terminated, and overflow of the storage tank 62 is also stopped (t9). In a case of further cleaning the outer wall surface (or inner and outer wall surfaces) of the dispensing nozzle 50 in the storage tank 62 after termination of lowering the dispensing nozzle 50, overflow is stopped after termination of the immersion cleaning of the dispensing nozzle 50 in the storage tank 62 (in such a case, the interval between t8 and t9 becomes longer by the time of immersion cleaning).

Thereafter, the dispensing nozzle 50 is started to be drawn up from the storage tank 62 by driving the nozzle transferring section 53 (t10), and the drawing of the dispensing nozzle 50 is completed at t12. The cleaning liquid L2 in the storage tank 62 is, as shown in FIG. 10(*e*), exhausted to the waste tank 62*c* by opening the electromagnetic valve 62*d* after the point t11 when the dispensing nozzle 50 is raised vertically by the nozzle transferring section 53 and drawn from the cleaning liquid L2 in the storage tank 62.

INDUSTRIAL APPLICABILITY

As described above, the nozzle cleaning method and nozzle cleaning device for cleaning a dispensing nozzle for suctioning and discharging a liquid of the present invention is useful in an analyzer which optically measures a reactant of a sample and a reagent and analyzes components of the sample.

The invention claimed is:

1. A nozzle cleaning device for cleaning a dispensing nozzle, comprising:
    a storage tank having an opening portion into which the dispensing nozzle is inserted;
    a discharge tube connected to a bottom portion of the storage tank;
    a first valve;
    a second valve;
    a cleaning liquid supply tank connected to the storage tank through at least one nozzle section above the opening portion and at least one nozzle section below the opening portion, wherein the at least one nozzle section above the opening portion is connected to the cleaning liquid supply tank and the first valve and the at least one nozzle section below the opening portion is connected to the cleaning liquid supply tank and the second valve; and
    an overflow tank into which cleaning liquid overflows from the storage tank; and
    a controlling section configured to:
        open the first and second valves to supply a cleaning liquid from the cleaning liquid supply tank to the storage tank through the at least one nozzle section above the opening portion and the at least one nozzle section below the opening portion, wherein the cleaning liquid overflows from the storage tank to the overflow tank;
        lower the dispensing nozzle into the storage tank through the opening portion to clean an outer wall surface of the dispensing nozzle;
        close the first and second valves to stop the supply of the cleaning liquid to the storage tank after the outer wall surface of the dispensing nozzle is clean; and
        raise the dispensing nozzle from the storage tank.

2. The nozzle cleaning device according to claim 1, wherein an opening portion of the overflow tank is formed to have a slope which inclines downwardly from the opening portion of the storage tank.

3. The nozzle cleaning device according to claim 1, wherein the controlling section is further configured to close the first and second valves to stop the supply of the cleaning liquid from the storage tank to the overflow tank, after liquid for preload including a sample discharged from the dispensing nozzle reaches the storage tank.

4. The nozzle cleaning device according to claim 3, wherein the controlling section is further configured to open the first and second valves to restart the flow of the cleaning liquid from the storage tank to the overflow tank, before a tip of the dispensing nozzle immerses into the storage tank.

5. The nozzle cleaning device according to claim 1, further comprising:
    a waste tank connected to the discharge tube via a third valve; and
    wherein the controlling section is further configured to open the third valve to exhaust the cleaning liquid from the storage tank through the discharge tube connected to the bottom portion of the storage tank into the waste tank.

6. The nozzle cleaning device according to claim 1, further comprising:
    a storing section that includes depth data and a sample type describing how the dispensing nozzle was used; and wherein the controlling section is further configured to determine a depth to lower the dispensing nozzle in the storage tank based on the depth data and the sample type.

7. The nozzle cleaning device according to claim 6, wherein the depth to lower the dispensing nozzle in the storage tank is higher than nozzle section below the aperture.

8. The nozzle cleaning device according to claim 1, further comprising:
a syringe connected to the dispensing nozzle, wherein the syringe includes a plunger connected to a plunger driving section via a motor, wherein the plunger driving section is configured to move the motor forward to apply a suction pressure to the dispensing nozzle and backward to apply a discharging pressure to the dispensing nozzle.

9. The nozzle cleaning device according to claim 8, further comprising:
a second cleaning liquid supply tank connected to the dispensing nozzle via the syringe, wherein a pump supplies cleaning liquid to the syringe from the second cleaning liquid supply tank.

10. The nozzle cleaning device according to claim 8, wherein the controlling section is further configured to:
before raising the dispensing nozzle, instruct the plunger driving section to suction and discharge the cleaning liquid from the storage tank through the dispensing nozzle to clean interior walls of the dispensing nozzle.

11. A nozzle cleaning device, comprising:
a storage tank including an aperture through which a dispensing nozzle is inserted;
an overflow tank into which cleaning liquid overflows from the storage tank;
a discharge tube connected to the storage tank;
a first valve;
a second valve;
a third valve;
a waste tank connected to the storage tank through the discharge tube and the third valve;
a cleaning liquid supply tank connected to the storage tank through a nozzle section below the aperture and a nozzle section above the aperture, wherein the nozzle section below the aperture is connected to the cleaning liquid supply tank and the first valve and wherein the cleaning liquid supply tank is connected to the nozzle section above the aperture and the second valve; and
a controlling section configured to:
open the first and second valves to supply a cleaning liquid from the cleaning liquid supply tank to the storage tank through the nozzle section below the aperture and the nozzle section above the aperture, wherein the cleaning liquid overflows from the storage tank to the overflow tank;
lower the dispensing nozzle into the storage tank through the aperture to clean an outer wall surface of the dispensing nozzle;
close the first and second valves to stop the supply of the cleaning liquid to the storage tank;
raise the dispensing nozzle from the storage tank while overflow of the cleaning liquid is stopped; and
open the third valve to exhaust the cleaning liquid from the storage tank through the discharge tube connected to the bottom portion of the storage tank.

12. The nozzle cleaning device according to claim 1, wherein the controlling section is further configured to:
instruct the dispensing nozzle to discharge liquid for preload while the cleaning liquid overflows from the storage tank to the overflow tank; and
close the first and second valves to stop the supply of the cleaning liquid to the storage tank after the liquid for preload is dispensed from the dispensing probe.

13. The nozzle cleaning device according to claim 11, further comprising:
a storing section that includes depth data and a sample type describing how the dispensing nozzle was used; and
wherein the controlling section is further configured to determine a depth to lower the dispensing nozzle in the storage tank based on the depth data and the same type.

14. The nozzle cleaning device according to claim 13, wherein the depth to lower the dispensing nozzle in the storage tank is higher than nozzle section below the aperture.

15. The nozzle cleaning device according to claim 11, wherein an opening portion of the overflow tank is formed to have a slope which inclines downwardly from the opening portion of the storage tank.

16. The nozzle cleaning device according to claim 11, further comprising
a syringe connected to the dispensing nozzle, wherein the syringe includes a plunger connected to a plunger driving section via a motor, wherein the plunger driving section is configured to move the motor forward to apply a suction pressure to the dispensing nozzle and backward to apply a discharging pressure to the dispensing nozzle.

17. The nozzle cleaning device according to claim 16, further comprising:
a second cleaning liquid supply tank connected to the dispensing nozzle via the syringe, wherein a pump supplies cleaning liquid to the syringe from the second cleaning liquid supply tank.

18. The nozzle cleaning device according to claim 16, wherein the controlling section is further configured to:
before raising the dispensing nozzle, instruct the plunger driving section to suction and discharge the cleaning liquid from the storage tank through the dispensing nozzle to clean interior walls of the dispensing nozzle.

* * * * *

UNITED STATES PATENT AND TRADEMARK OFFICE
CERTIFICATE OF CORRECTION

| | |
|---|---|
| PATENT NO. | : 8,764,912 B2 |
| APPLICATION NO. | : 12/881118 |
| DATED | : July 1, 2014 |
| INVENTOR(S) | : Akihisa Kuroda |

It is certified that error appears in the above-identified patent and that said Letters Patent is hereby corrected as shown below:

In the Claims

In Claim 12 in Column 20, line 11 please replace "12. The nozzle cleaning device according to claim 1," with -- 12. The nozzle cleaning device according to claim 11, --

Signed and Sealed this
Twenty-first Day of October, 2014

Michelle K. Lee
*Deputy Director of the United States Patent and Trademark Office*